(12) United States Patent
Cage et al.

(10) Patent No.: US 10,107,784 B2
(45) Date of Patent: Oct. 23, 2018

(54) ELECTROMAGNETIC TRANSDUCER

(71) Applicant: CONCENTRIC METER CORPORATION, Longmont, CO (US)

(72) Inventors: Donald R. Cage, Longmont, CO (US); Michael N. Schott, Loveland, CO (US); Kristian S. Schartau, Erie, CO (US)

(73) Assignee: Concentric Meter Corporation, Longmont, CO (US)

( * ) Notice: Subject to any disclaimer, the term of this patent is extended or adjusted under 35 U.S.C. 154(b) by 64 days.

(21) Appl. No.: 14/981,402

(22) Filed: Dec. 28, 2015

(65) Prior Publication Data
US 2016/0187300 A1 Jun. 30, 2016

Related U.S. Application Data

(60) Provisional application No. 62/097,221, filed on Dec. 29, 2014.

(51) Int. Cl.
*G01N 29/24* (2006.01)
*G01N 29/02* (2006.01)
(Continued)

(52) U.S. Cl.
CPC ....... *G01N 29/2412* (2013.01); *G01F 1/8422* (2013.01); *G01F 1/8459* (2013.01);
(Continued)

(58) Field of Classification Search
CPC .. G01N 29/2412; G01N 29/222; G01N 29/02; G01N 2291/02416;
(Continued)

(56) References Cited

U.S. PATENT DOCUMENTS 1,175,586 A 3/1916 Beyler
2,215,566 A 9/1940 Schaaf, Jr.
(Continued)

FOREIGN PATENT DOCUMENTS

EP 0222503 5/1987
EP 2612130 9/2014
(Continued)

OTHER PUBLICATIONS

Written Opinion of the International Searching Authority for co-owned PCT patent application No. PCT/US2015/067710 dated Apr. 29, 2016, 10 pages.
(Continued)

*Primary Examiner* — Manish S Shah
*Assistant Examiner* — Suman K Nath
(74) *Attorney, Agent, or Firm* — Trenner Law Firm, LLC; Mark D. Trenner

(57) ABSTRACT

An electromagnetic transducer is disclosed. An example electromagnetic transducer may be provided for a fluid parameter meter. The example electromagnetic transducer may include at least one permanent magnet, a first armature mounted in magnetic cooperation with the permanent magnet, and a second armature mounted in magnetic cooperation with the permanent magnet. The first and the second armatures are arranged to interact with a third armature in magnetic cooperation with the first armature and the second armature. The example electromagnetic transducer may also include at least one electric coil mounted in cooperation with the magnetic field so that electric current through the electric coil to vary the vibratory forces. The example electromagnetic transducer may include an electronic module to control electric current and vibratory forces on a vibrating element of the fluid parameter meter.

20 Claims, 12 Drawing Sheets

(51) Int. Cl.
*G01N 29/22* (2006.01)
*H02K 33/16* (2006.01)
*G01F 1/84* (2006.01)

(52) U.S. Cl.
CPC ........... *G01N 29/02* (2013.01); *G01N 29/222* (2013.01); *H02K 33/16* (2013.01); *G01N 2291/022* (2013.01); *G01N 2291/02416* (2013.01); *G01N 2291/101* (2013.01)

(58) Field of Classification Search
CPC ........ G01N 2291/101; G01N 2291/022; G01F 1/8459; G01F 1/8422; H02K 33/16
USPC .......................................................... 73/643
See application file for complete search history.

(56) References Cited

U.S. PATENT DOCUMENTS

| | | |
|---|---|---|
| 2,340,992 A | 2/1944 | Siegel |
| 3,021,711 A | 2/1962 | Arvidson |
| 3,164,987 A | 1/1965 | Davidson |
| 3,218,851 A | 11/1965 | Anatole |
| 3,225,588 A | 12/1965 | Jacques |
| 3,648,512 A | 3/1972 | Abbotts |
| 3,677,067 A | 7/1972 | Miller et al. |
| 3,741,000 A | 6/1973 | Miller |
| 3,763,692 A | 10/1973 | Agar |
| 3,955,401 A | 5/1976 | Catherall |
| 3,956,922 A | 5/1976 | November |
| 3,958,446 A | 5/1976 | November |
| 3,967,490 A | 7/1976 | Brady |
| 3,981,183 A | 9/1976 | Banks |
| 3,983,744 A | 10/1976 | Agar |
| 3,984,895 A | 10/1976 | Grice |
| 3,999,421 A | 12/1976 | Creswick |
| 4,007,627 A | 2/1977 | Stansfeld |
| 4,015,470 A | 4/1977 | Morrison |
| 4,020,330 A | 4/1977 | Du Bae |
| 4,023,400 A | 5/1977 | November |
| 4,024,759 A | 5/1977 | Klinger |
| 4,037,459 A | 7/1977 | Schlatter |
| 4,037,460 A | 7/1977 | November et al. |
| 4,037,461 A | 7/1977 | Miller |
| 4,041,769 A | 8/1977 | November |
| 4,063,448 A | 12/1977 | Agar |
| 4,064,738 A | 12/1977 | November |
| 4,064,739 A | 12/1977 | November et al. |
| 4,074,562 A | 2/1978 | North |
| 4,084,425 A | 4/1978 | Bae |
| 4,096,745 A | 6/1978 | Rivkin |
| 4,114,423 A | 9/1978 | Wenger |
| 4,117,716 A | 10/1978 | Simon |
| 4,127,028 A | 11/1978 | Cox |
| 4,129,031 A | 12/1978 | Tehon |
| 4,132,110 A | 1/1979 | Muramoto |
| 4,135,383 A | 1/1979 | November |
| 4,151,743 A | 5/1979 | Ghahramani |
| 4,158,959 A | 6/1979 | Blair |
| 4,170,128 A | 10/1979 | Kratky |
| 4,177,669 A | 12/1979 | Wenger |
| 4,187,721 A | 2/1980 | Smith |
| 4,192,184 A | 3/1980 | Cox |
| 4,193,291 A | 3/1980 | Lynnworth |
| 4,194,385 A | 3/1980 | November |
| 4,215,566 A | 8/1980 | Ghahramani |
| 4,217,774 A | 8/1980 | Agar |
| 4,232,544 A | 11/1980 | Stansfeld |
| 4,235,099 A | 11/1980 | Ishizaka |
| 4,240,285 A | 12/1980 | Langdon |
| 4,262,523 A | 4/1981 | Stansfeld |
| 4,265,125 A | 5/1981 | Mahany |
| 4,275,585 A | 6/1981 | Buzzell |
| 4,282,742 A | 8/1981 | Kalotay et al. |
| 4,283,936 A | 8/1981 | November |
| 4,297,608 A | 10/1981 | Jensen |
| 4,297,872 A | 11/1981 | Ikeda |
| 4,345,456 A | 8/1982 | Ponzi |
| 4,349,881 A | 9/1982 | November |
| 4,354,377 A | 10/1982 | Stansfeld |
| 4,361,052 A | 11/1982 | Nicol et al. |
| 4,362,048 A | 12/1982 | Agar |
| 4,411,161 A | 10/1983 | November |
| RE31,450 E | 11/1983 | Smith |
| 4,420,983 A | 12/1983 | Langdon |
| 4,429,564 A | 2/1984 | Ikeda |
| 4,442,700 A | 4/1984 | Swoboda |
| 4,445,389 A | 5/1984 | Potzick |
| 4,449,414 A | 5/1984 | Coates |
| 4,466,272 A | 8/1984 | Stansfeld |
| 4,470,294 A | 9/1984 | Hamel |
| 4,480,461 A | 11/1984 | Ponzi |
| 4,491,009 A | 1/1985 | Ruesch |
| 4,493,215 A | 1/1985 | Gast |
| 4,495,818 A | 1/1985 | Ikeda |
| 4,522,068 A | 6/1985 | Smith |
| 4,524,610 A | 6/1985 | Fitzgerald |
| 4,526,480 A | 7/1985 | Ward |
| 4,530,234 A | 7/1985 | Cullick |
| 4,546,641 A | 10/1985 | Nguyen |
| 4,550,768 A | 11/1985 | McMullen |
| 4,566,312 A | 1/1986 | Collins |
| 4,574,639 A | 3/1986 | Ward |
| 4,583,393 A | 4/1986 | Sweet |
| 4,601,200 A | 7/1986 | Stoffelen |
| 4,602,498 A | 7/1986 | Glikberg |
| 4,608,869 A | 9/1986 | Lerner |
| 4,614,115 A | 9/1986 | Pelletier |
| 4,624,129 A | 11/1986 | Haynes |
| 4,628,739 A | 12/1986 | Bruggen et al. |
| 4,640,128 A | 2/1987 | Lewis |
| 4,655,075 A | 4/1987 | Aibert |
| 4,662,221 A | 5/1987 | Kaine |
| 4,671,099 A | 6/1987 | Lazarre |
| 4,674,322 A | 6/1987 | Stangeland |
| 4,677,842 A | 7/1987 | Piche |
| 4,679,947 A | 7/1987 | Miller |
| 4,683,752 A | 8/1987 | Bradshaw |
| 4,691,557 A | 9/1987 | Dunn et al. |
| 4,754,640 A | 7/1988 | Fitzgerald |
| 4,770,042 A | 9/1988 | Cobb |
| 4,770,043 A | 9/1988 | Cobb |
| 4,783,987 A | 11/1988 | Hager |
| 4,788,466 A | 11/1988 | Paul |
| 4,796,468 A | 1/1989 | Blake-Coleman |
| 4,802,360 A | 2/1989 | Maier |
| 4,803,867 A | 2/1989 | Dahlin |
| 4,811,592 A | 3/1989 | Miura |
| 4,815,323 A | 3/1989 | Ellinger |
| 4,827,746 A | 5/1989 | Kawaguchi |
| 4,838,084 A | 6/1989 | Leopold |
| 4,848,139 A | 7/1989 | Blake-Coleman |
| 4,854,172 A | 8/1989 | Lemaster |
| 4,872,335 A | 10/1989 | Tsuruoka |
| 4,876,879 A | 10/1989 | Ruesch |
| 4,890,480 A | 1/1990 | Young |
| 4,893,496 A | 1/1990 | Bau |
| 4,905,499 A | 3/1990 | Miura |
| 4,909,068 A | 3/1990 | Miura |
| 4,912,962 A | 4/1990 | Kawaguchi |
| 4,922,745 A | 5/1990 | Rudkin |
| 4,934,177 A | 6/1990 | Cuthbertson |
| 4,958,332 A | 9/1990 | Tellerman |
| 4,959,228 A | 9/1990 | Skrgatic |
| 4,961,345 A | 10/1990 | Tsuruoka |
| 4,962,671 A | 10/1990 | Stansfeld |
| 4,991,124 A | 2/1991 | Kline |
| 4,996,656 A | 2/1991 | Hedrick |
| 4,996,871 A | 3/1991 | Romano |
| 5,000,050 A | 3/1991 | Hetrick |
| 5,005,400 A | 4/1991 | Lew |
| 5,025,656 A | 6/1991 | Wright |
| 5,048,323 A | 9/1991 | Stansfeld |
| 5,067,344 A | 11/1991 | Fitzgerald |
| 5,074,148 A | 12/1991 | Lew |

(56) References Cited

U.S. PATENT DOCUMENTS

| | | |
|---|---|---|
| 5,078,011 A | 1/1992 | Morkun |
| 5,117,146 A | 5/1992 | Martin |
| 5,157,962 A | 10/1992 | Fitzgerald |
| 5,201,215 A | 4/1993 | Granstaff |
| 5,214,955 A | 6/1993 | Yost |
| 5,218,858 A | 6/1993 | Jen |
| 5,237,853 A | 8/1993 | Cassaday |
| 5,253,522 A | 10/1993 | Nyce |
| 5,253,533 A | 10/1993 | Lam |
| 5,271,267 A | 12/1993 | Baumoel |
| 5,295,084 A | 3/1994 | Arunachalam |
| 5,323,638 A | 6/1994 | Langdon |
| 5,332,550 A | 7/1994 | Booker |
| 5,339,258 A | 8/1994 | Stabinger |
| 5,345,811 A | 9/1994 | Alexandrovich |
| 5,359,541 A | 10/1994 | Pope |
| 5,359,897 A | 11/1994 | Hamstead |
| 5,363,691 A | 11/1994 | Gallagher |
| 5,365,778 A | 11/1994 | Sheen |
| 5,383,349 A | 1/1995 | Blake-Coleman |
| 5,386,714 A | 2/1995 | Dames |
| 5,402,670 A | 4/1995 | Wicnienski |
| 5,471,873 A | 12/1995 | Nyce |
| 5,473,949 A | 12/1995 | Cage |
| 5,477,726 A | 12/1995 | Stabinger |
| 5,531,091 A | 7/1996 | Gademann et al. |
| 5,533,381 A | 7/1996 | Seale |
| 5,569,844 A | 10/1996 | Sowerby |
| 5,576,500 A | 11/1996 | Cage et al. |
| 5,606,113 A | 2/1997 | Sheen et al. |
| 5,670,709 A | 9/1997 | Gallagher |
| 5,675,071 A | 10/1997 | Cody |
| 5,687,100 A | 11/1997 | Buttler |
| 5,698,773 A | 12/1997 | Blom |
| 5,708,191 A | 1/1998 | Greenwood |
| 5,728,952 A | 3/1998 | Yao |
| 5,741,971 A | 4/1998 | Lacy |
| 5,753,827 A | 5/1998 | Cage |
| 5,804,698 A | 9/1998 | Belonenko |
| 5,814,739 A | 9/1998 | Van Cleve |
| 5,837,885 A | 11/1998 | Goodbread |
| 5,886,250 A | 3/1999 | Greenwood |
| 5,900,535 A | 5/1999 | Doe |
| 5,907,104 A | 5/1999 | Cage |
| 5,965,824 A | 10/1999 | Kishiro |
| 5,974,858 A | 11/1999 | Francisco |
| 5,987,966 A | 11/1999 | Fontanille |
| 6,006,589 A | 12/1999 | Rodahl |
| 6,029,501 A | 2/2000 | Nishino |
| 6,044,694 A | 4/2000 | Anderson |
| 6,050,141 A | 4/2000 | Tell |
| 6,073,495 A | 6/2000 | Stadler |
| 6,082,180 A | 7/2000 | Greenwood |
| 6,082,181 A | 7/2000 | Greenwood |
| 6,151,956 A | 11/2000 | Takahashi |
| 6,182,499 B1 | 2/2001 | McFarland |
| 6,189,367 B1 | 2/2001 | Smith |
| 6,247,354 B1 | 6/2001 | Vig |
| 6,269,686 B1 | 8/2001 | Hahn |
| 6,286,361 B1 | 9/2001 | Jones |
| 6,305,212 B1 | 10/2001 | Drzewiecki |
| 6,311,549 B1 | 11/2001 | Thundat |
| 6,314,791 B1 | 11/2001 | Rapp |
| 6,327,914 B1 | 12/2001 | Dutton |
| 6,336,353 B2 | 1/2002 | Matsiev |
| 6,360,606 B2 | 3/2002 | Hirota |
| 6,360,610 B1 | 3/2002 | Jarzynski |
| 6,370,939 B2 | 4/2002 | Smith |
| 6,389,877 B1 | 5/2002 | Takeuchi |
| 6,393,895 B1 | 5/2002 | Matsiev |
| 6,397,661 B1 | 6/2002 | Grimes |
| 6,401,519 B1 | 6/2002 | McFarland |
| 6,450,013 B1 | 9/2002 | Gallagher |
| 6,494,079 B1 | 12/2002 | Matsiev |
| 6,513,365 B1 | 2/2003 | Bruetting |
| 6,543,274 B1 | 4/2003 | Herrmann |
| 6,546,784 B2 | 4/2003 | Bilmes et al. |
| 6,557,416 B2 | 5/2003 | Chang |
| 6,634,214 B1 | 10/2003 | Thurston |
| 6,647,764 B1 | 11/2003 | Paul |
| 6,651,484 B2 | 11/2003 | Fiebelkorn |
| 6,684,683 B2 | 2/2004 | Potyrailo |
| 6,688,176 B2 | 2/2004 | Storm |
| 6,722,200 B2 | 4/2004 | Roukes |
| 6,732,570 B2 | 5/2004 | Francisco |
| 6,763,698 B2 | 7/2004 | Greenwood |
| 6,786,077 B2 | 9/2004 | Baumoel |
| 6,813,928 B2 | 11/2004 | Blakley |
| 6,826,949 B1 | 12/2004 | Berndt |
| 6,845,663 B2 | 1/2005 | Lopatin |
| 6,848,299 B2 | 2/2005 | Paul |
| 6,874,355 B2 | 4/2005 | Kornfeldt |
| 6,874,356 B2 | 4/2005 | Kornfeldt |
| 6,885,491 B2 | 4/2005 | Ross-Messemer |
| 6,904,786 B2 | 6/2005 | Matsiev |
| 6,912,904 B2 | 7/2005 | Storm |
| 6,918,283 B2 | 7/2005 | Berstis |
| 6,924,642 B1 * | 8/2005 | Cho ................ B06B 1/08 324/220 |
| 6,928,877 B2 | 8/2005 | Carlson |
| 6,938,462 B2 | 9/2005 | Jakoby |
| 6,957,565 B2 | 10/2005 | Matsiev |
| 6,971,259 B2 | 12/2005 | Gysling |
| 6,986,276 B2 | 1/2006 | Gysling |
| 7,024,917 B2 | 4/2006 | DiFoggio |
| 7,059,169 B2 | 6/2006 | Cummings |
| 7,059,171 B2 | 6/2006 | Gysling |
| 7,059,172 B2 | 6/2006 | Gysling |
| 7,073,370 B2 | 7/2006 | Matsiev |
| 7,117,717 B2 | 10/2006 | Mattar |
| 7,134,320 B2 | 11/2006 | Gysling |
| 7,152,460 B2 | 12/2006 | Gysling |
| 7,191,638 B2 | 3/2007 | Lopatin |
| 7,216,543 B2 | 5/2007 | Paik |
| 7,254,987 B2 | 8/2007 | Tinianov et al. |
| 7,257,987 B2 | 8/2007 | O'Brien |
| 7,257,988 B2 | 8/2007 | Mattar et al. |
| 7,334,452 B2 | 2/2008 | Matsiev |
| 7,360,399 B2 | 4/2008 | Schmidt |
| 7,380,439 B2 | 6/2008 | Gysling |
| 7,399,609 B2 | 7/2008 | Lakshmi |
| 7,409,851 B2 | 8/2008 | Ilic |
| 7,426,866 B2 | 9/2008 | Van Tuyl |
| 7,437,909 B2 | 10/2008 | Wagner |
| 7,454,981 B2 | 11/2008 | Gysling |
| 7,523,640 B2 | 4/2009 | DiFoggio |
| 7,530,268 B2 | 5/2009 | Lopatin |
| 7,549,319 B2 | 6/2009 | Headrick |
| 7,552,619 B2 | 6/2009 | Andle |
| 7,562,557 B2 | 7/2009 | Bennett |
| 7,581,429 B2 | 9/2009 | Sparks et al. |
| 7,596,987 B2 | 10/2009 | Gysling |
| 7,597,008 B2 | 10/2009 | Patten |
| 7,610,795 B2 | 11/2009 | Bitto |
| 7,669,458 B2 | 3/2010 | Commuri |
| 7,689,370 B2 | 3/2010 | Grosser |
| 7,735,353 B2 | 6/2010 | Wagner |
| 7,788,979 B2 | 9/2010 | Vetelino |
| 7,831,400 B2 | 11/2010 | Stack |
| 7,874,199 B2 | 1/2011 | Chaudoreille |
| 7,878,044 B2 | 2/2011 | Andle |
| 7,908,903 B2 | 3/2011 | Wagner |
| 7,913,556 B2 | 3/2011 | Hsu |
| 7,921,691 B2 | 4/2011 | DiFoggio et al. |
| 7,941,284 B1 | 5/2011 | Glaudel |
| 7,958,772 B2 | 6/2011 | Permuy |
| 7,966,882 B2 | 6/2011 | Greenwood |
| 8,020,428 B2 | 9/2011 | Snieder |
| 8,087,284 B2 | 1/2012 | Babcock et al. |
| 8,166,801 B2 | 5/2012 | Sinha |
| 8,170,812 B2 | 5/2012 | Straub |
| 8,173,283 B2 | 5/2012 | Furukawa |
| 8,190,338 B2 | 5/2012 | Commuri |
| 8,215,170 B2 | 7/2012 | Tao |

(56) References Cited

U.S. PATENT DOCUMENTS

| | | | |
|---|---|---|---|
| 8,281,646 | B2 | 10/2012 | Waid et al. |
| 8,322,194 | B2 | 12/2012 | Muller |
| 8,322,210 | B2 | 12/2012 | Abele |
| 8,333,106 | B2 | 12/2012 | Wagner |
| 8,408,045 | B2 | 4/2013 | Forrer |
| 8,434,350 | B2 | 5/2013 | Urban et al. |
| 8,448,496 | B2 | 5/2013 | Huang et al. |
| 8,511,144 | B2 | 8/2013 | Goravar |
| 8,601,857 | B2 | 12/2013 | Ichihashi |
| 8,707,763 | B2 | 4/2014 | Viachaslau |
| 9,429,458 | B2 | 8/2016 | Hussain |
| 9,752,911 | B2 | 9/2017 | Cage et al. |
| 2002/0033054 | A1* | 3/2002 | Frey ................ G01F 1/586 73/861.12 |
| 2003/0230150 | A1* | 12/2003 | Drahm ................ G01F 1/58 73/861.32 |
| 2004/0000197 | A1 | 1/2004 | Gysling |
| 2004/0226386 | A1 | 11/2004 | Gysling et al. |
| 2006/0031030 | A1 | 2/2006 | Bennett et al. |
| 2007/0261407 | A1 | 11/2007 | Bin-Nun et al. |
| 2010/0024569 | A1 | 2/2010 | Ehrenberg et al. |
| 2010/0280757 | A1 | 11/2010 | Agar et al. |
| 2011/0016988 | A1 | 1/2011 | Tombs et al. |
| 2011/0023625 | A1 | 2/2011 | Weinstein |
| 2011/0160893 | A1 | 6/2011 | Rothman et al. |
| 2011/0199603 | A1 | 8/2011 | Yoshioka et al. |
| 2016/0187176 | A1 | 6/2016 | Cage |
| 2016/0332129 | A1 | 11/2016 | Schott |
| 2016/0334316 | A1 | 11/2016 | Cage |
| 2017/0205373 | A1 | 7/2017 | Cage et al. |

FOREIGN PATENT DOCUMENTS

| | | |
|---|---|---|
| JP | 2007-047071 | 2/2007 |
| JP | 2010-038752 | 2/2010 |
| WO | WO2006/107900 | 10/2006 |
| WO | WO2012/156980 | 11/2012 |
| WO | WO 2012030353 | 10/2014 |
| WO | WO 2014172111 | 10/2014 |

OTHER PUBLICATIONS

Written Opinion of the International Searching Authority for co-owned PCT patent application No. PCT/US2015/067716 dated Apr. 6, 2016, 10 pages.

Written Opinion of the InternationalInternatiional Searching Authority for co-owned PCT patent application No. PCT/US2016/32200 dated Aug. 16, 2016, 9 pages.

Written Opinion of the International Searching Authority for co-owned PCT patent application No. PCT/US2016/32204 dated Aug. 16, 2016, 11 pages.

Written Opinion of the International Searching Authority for co-owned PCT patent application No. PCT/US2015/067710, dated Jul. 13, 2017, 12 pages.

Written Opinion of the International Searching Authority for co-owned PCT patent application No. PCT/US2015/067716, dated Jul. 13, 2017, 12 pages.

PCT International Preliminary Report for PCT application No. PCT/US2016/032200, dated Aug. 16, 2016, 7 pages.

PCT International Preliminary Report for PCT application No. PCT/US2016/032204, dated Sep. 27, 2016, 7 pages.

English abstract for JP2007-047071 dated Feb. 22, 2007, 2 pages.

English abstract for JP2010-038752 dated Feb. 18, 2010, 2 pages.

International Search Report for PCT/US2015/067710, dated Apr. 6, 2016, 3 pages.

International Search Report for PCT/US2015/067716, dated Apr. 29, 2016, 3 pages.

Extended European Search Report, dated Jun. 22, 2018, 9 pages.

* cited by examiner

ELECTROMAGNETIC TRANSDUCER

CROSS REFERENCE TO RELATED APPLICATIONS

This application claims the priority benefit of U.S. Provisional Patent Application No. 62/097,221 filed Dec. 29, 2014 titled "Electromagnetic Transducer For Causing Or Sensing Vibratory Forces On A Vibrating Element In A Vibrating Element-Type Fluid Parameter Meter" of Donald R. Cage, et al., incorporated by reference in its entirety as though fully set forth herein.

BACKGROUND

By passing an undirected magnetic field through the wall of a pipe or conduit, the magnetic field is largely attenuated by the distance traveled and due to its natural field shape, and by eddy current losses that can occur in electrically or magnetically conductive materials that make up the wall of the pipe or conduit, or are proximate to the wall of the fluid carrying conduit, and in the armatures themselves. This attenuation limits the magnitude of the force and power available to vibrate the immersed vibrating element in high viscosity fluids such as hydraulic-fracturing fluids ("fracking fluids"), oil well cementing fluids, for example in the thick walled high pressure conduits which are common in the hydraulic-fracturing and oil well drilling industries.

In addition, magnetic particles (e.g., rust particles or iron filings) in a fluid stream are often attracted to and adhere to the electromagnetic drivers and sensors. These entrapped particles cause measurement errors for the immersed vibrating element type meter because of the added weight, magnetic permeability, electrical conductivity, and damping properties of the adherent particles.

DETAILED DESCRIPTION

Figure 1A:
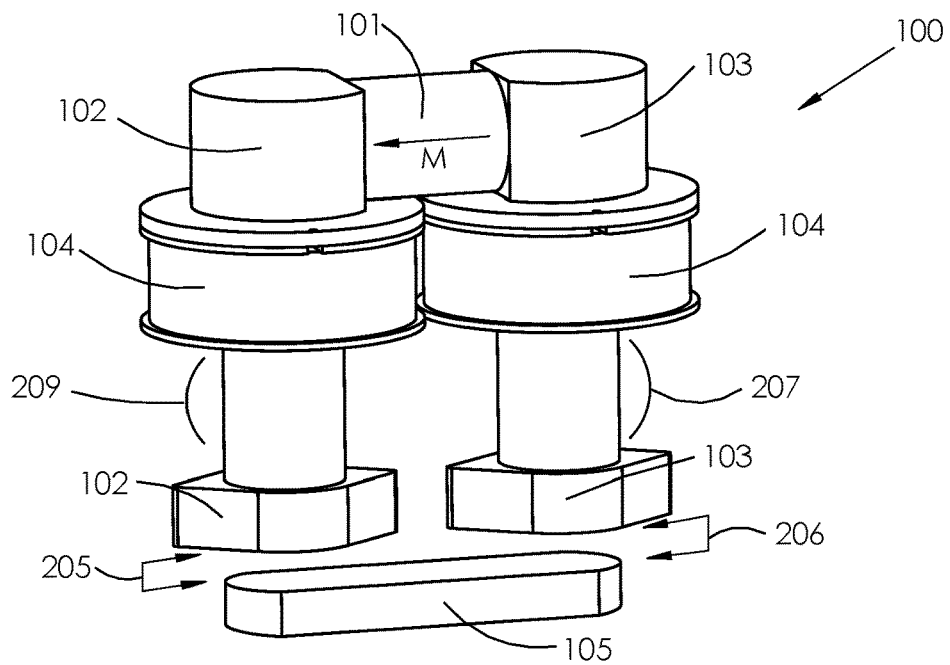
FIG. 1A is an isometric view of an example transducer assembly.

In the field of immersed vibrating element type meters for measuring fluid parameters of density, viscosity, flow rate, and the like, electromagnetic transducers are often implemented to cause and to detect the requisite vibration of the immersed vibrating element. However, the current art is generally inadequate for higher power levels for vibrating large sizes of immersed vibrating elements, especially in high viscosity and abrasive fluids such as hydraulic-fracturing fluids ("fracking fluids"), oil well cementing fluids, slurries and the like.

An electromagnetic transducer is disclosed herein, e.g., as it may be provided for a fluid parameter meter. In an example, the electromagnetic transducer includes at least one permanent magnet, a first armature mounted in magnetic cooperation with the permanent magnet, and a second armature mounted in magnetic cooperation with the permanent magnet. The first and the second armatures are arranged to interact with a third armature in magnetic cooperation with the first armature and the second armature. The example electromagnetic transducer may also include at least one electric coil mounted in cooperation with the magnetic field so that electric current through the electric coil to vary the vibratory forces. The example electromagnetic transducer may include an electronic module to control electric current and vibratory forces on a vibrating element of the fluid parameter meter.

In an example, the electromagnetic transducer may be provided for an immersed vibrating element type fluid parameter meter, that can convey large magnetic fields through large thicknesses of the fluid carrying outer conduit wall, can deliver those large magnetic fields directly to the immersed vibrating element, and can be cleaned of any adherent particles which have become attached thereto.

In an example, the electromagnetic transducer may be provided in conjunction with an immersed vibrating element type fluid parameter meter having an outer conduit, and a vibrating element mounted therein. The example electromagnetic transducer may include a permanent magnet, one or more coils mounted outside the fluid conduit, and first and second armatures. The first armature is made of magnetically permeable material. It is magnetically attached at its proximal end to one end of the permanent magnet, passes through at least one coil, and passes through the fluid conduit wall at a first location, so that its distal end is immersed in the fluid near either the vibrating element acting as a third armature, or a separate third armature mounted in association with the vibrating element, thereby creating a first gap, and it is sealed to the fluid conduit wall to prevent any leakage of the fluid. The second armature is also made of magnetically permeable material. It is attached at its proximal end to the opposite end of the permanent magnet, and passes through at least one coil, and passes through the fluid conduit wall at a second location, so that its distal end is immersed in the fluid near either the vibrating element acting as the third armature, or a separate third armature mounted in association with the vibrating element, thereby creating a second gap, and it is sealed to the fluid conduit wall to prevent any leakage of the fluid there through. Both first and second armatures distal ends terminate in the fluid near and in magnetic cooperation with, the vibrating element acting as the third armature, or near the separate third armature attached to the vibrating element, thereby forming a magnetic circuit including a first and second gap between the third armature, and the first and second armatures.

The permanent magnet causes a magnetic field to pass through the armatures in the magnetic circuit, which causes a pulling force to be applied across the gaps, between the first and second armatures, and the third armature, resulting in a pulling force on the immersed vibrating element. By bringing the armatures through the conduit wall and through the fluid to be measured directly to the vibrating element acting as a third armature, or a separate third armature mounted in association with the vibrating element, very large magnetic fields and magnetic forces can be thereby delivered which are much larger than prior art systems.

To further reduce electrical and or magnetic loses, loss reduction methods and apparatus can be provided in conjunction with the armatures which further improve efficiency. One example configuration for loss reduction includes non-electrically conductive and or non-magnetically permeable material for the outer conduit and or any parts that are proximate to the armatures. Another example configuration for loss reduction is a non-conductive and or non-magnetic material in-between and around the armatures where they pass through the outer conduit, thereby reducing eddy-current losses and magnetic attenuation that otherwise may occur during operation. Another example configuration for loss reduction is to modify the shape of the outer conduit to increase its resistivity especially in the area between and around the armatures. This shape modification can be provided by removing material by machining, or forming, or by conduit configuration or other methods.

The example electromagnetic transducer may be implemented as a vibration driver. In an example, alternating electrical current may be applied by an electronic control module in association with a drive amplifier to the one or more coils, causing an alternating magnitude of the magnetic field, and the resulting pulling force. This alternating current and its resulting alternating force is caused to be synchronized in the appropriate phase and frequency with the desired natural vibration mode shape of the immersed vibrating element to reinforce the natural vibration and to increase its amplitude and to maintain that amplitude at a prescribed value.

The example electromagnetic transducer may be implemented as a vibration sensor. In an example, the vibrating element vibration causes an alternating gap distance which alternates the permeability of the entire magnetic circuit thereby alternating the magnetic field passing there through. The alternating magnetic field passing through the one or more coils causes an alternating voltage to occur in the one or more coils. This alternating voltage is measured by an electronic control module in cooperation with a sensing amplifier and is representative of the vibration motion. The electronic control module implements the alternating voltage to create an output signal representative of the vibration motion, and is provided as feedback to amplify and control the requisite vibration of the vibrating element.

According to this example configuration, large magnetic fields and large magnetic forces can be transmitted directly to the immersed vibrating element even through very thick conduit walls. When the transducer is configured as a motion sensor, high sensitivities are achieved resulting in high signal strength through very thick outer conduit wall thicknesses. This handles the vibration of large immersed vibrating elements that are mounted within thick walled conduits, and enables sufficient forces to be transmitted to vibrate vibrating elements operating in high viscosity fluids such as fracking fluids and cementing fluids and slurries.

In an example, the electromagnetic transducer can be cleaned of adherent magnetic particles. Due to the magnetic field from the permanent magnet (or from an electromagnet as explained hereinafter), magnetic particles such as rust or iron filings flowing with the fluid can become attached to the armatures, thereby interfering with the natural vibration of the vibrating element and causing errors. This can be addressed by applying an electrical current in the coils to cause a magnetic field in opposition to the field of the permanent magnet, forcing the total magnetic field in the gap and in the third armature to near zero. This releases any attached magnetic particles to be washed away by the flowing fluid. This cleaning cycle can be repeated as necessary or as desired.

In another example, no permanent magnet is provided in the magnetic circuit. Instead, a current is directed through the one or more coils to create a magnetic field similar to the magnetic field of the permanent magnet. Directing current through the one or more coils to create a magnetic field is similar to replacing the permanent magnet with an electro magnet. Without a permanent magnet in the magnetic circuit, adherent magnetic particles can be cleaned by temporarily removing the electrical current causing the magnetic field so that the magnetic field returns to near zero. This enables any adherent magnetic particles to be loosened and washed away by the flowing fluid.

Before continuing, it is noted that as used herein, the terms "includes" and "including" mean, but is not limited to, "includes" or "including" and "includes at least" or "including at least." The term "based on" means "based on" and "based at least in part on."

Figure 1B:
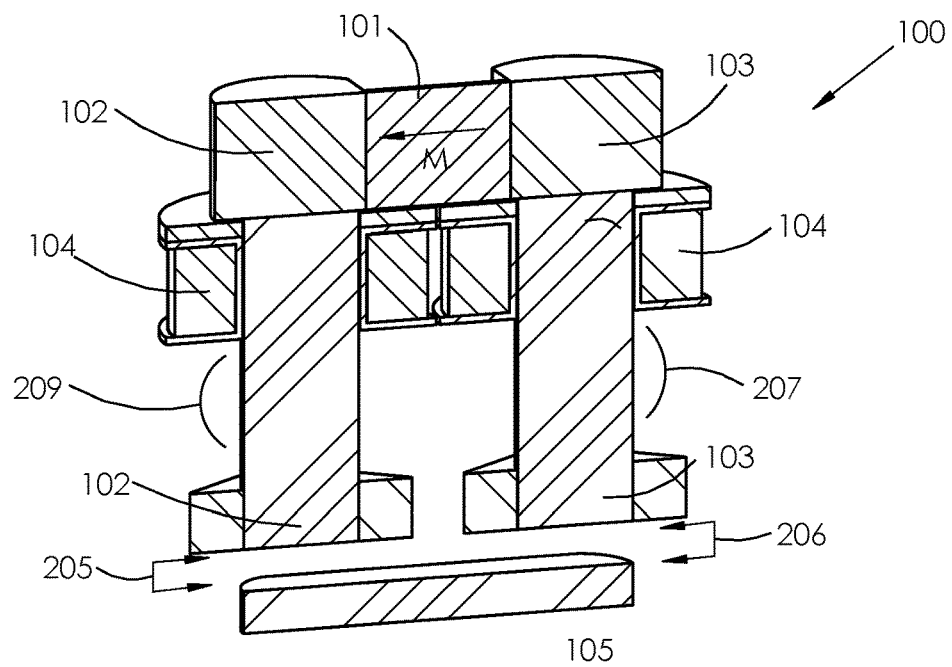
FIG. 1B is a cross section view of the example transducer assembly of FIG. 1.
Figure 1C:
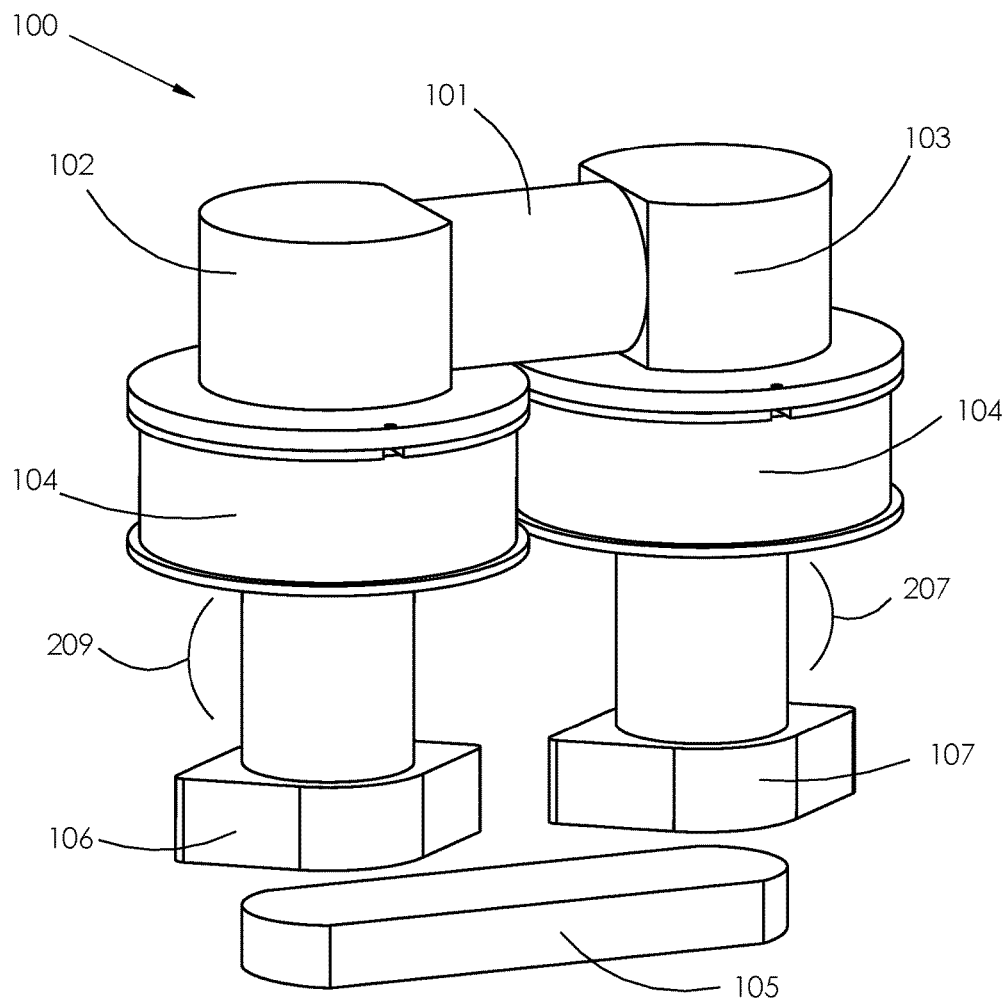
FIG. 1C is similar to FIG. 1A, except that hydrodynamic shaped armatures have been added in FIG. 10 to minimize abrasion.

FIG. 1A is an isometric view of an example transducer assembly 100. FIG. 1B is a cross section view of the example transducer assembly 100 of FIG. 1. FIG. 1C is similar to FIG. 1A, except that hydrodynamic shaped armatures 106 and 107 have been added in FIG. 10 to minimize abrasion.

Figure 2A:
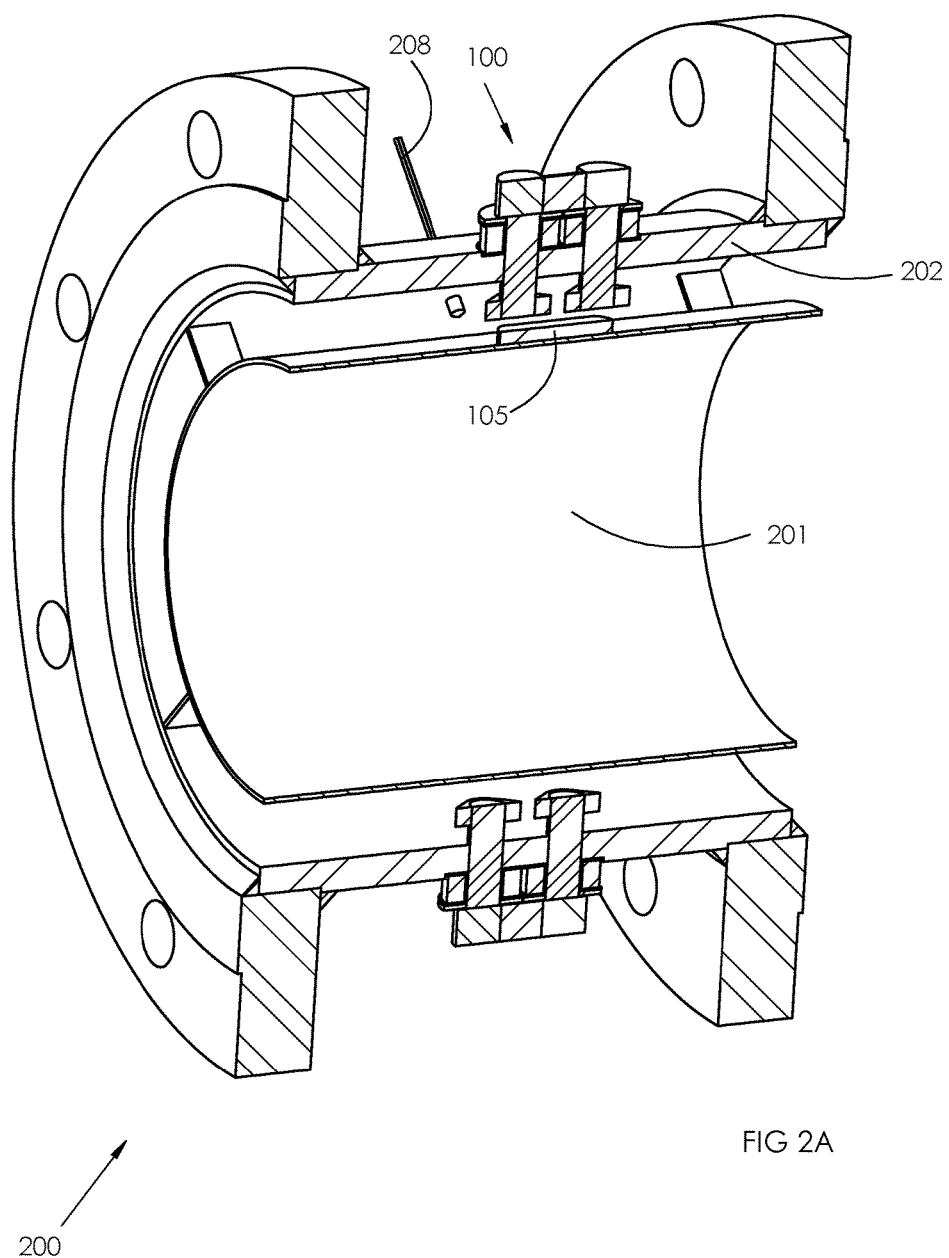
FIG. 2A is a cross section view of the example transducer assembly of FIG. 1 assembled into an immersed vibrating element type fluid parameter meter.
Figure 2B:
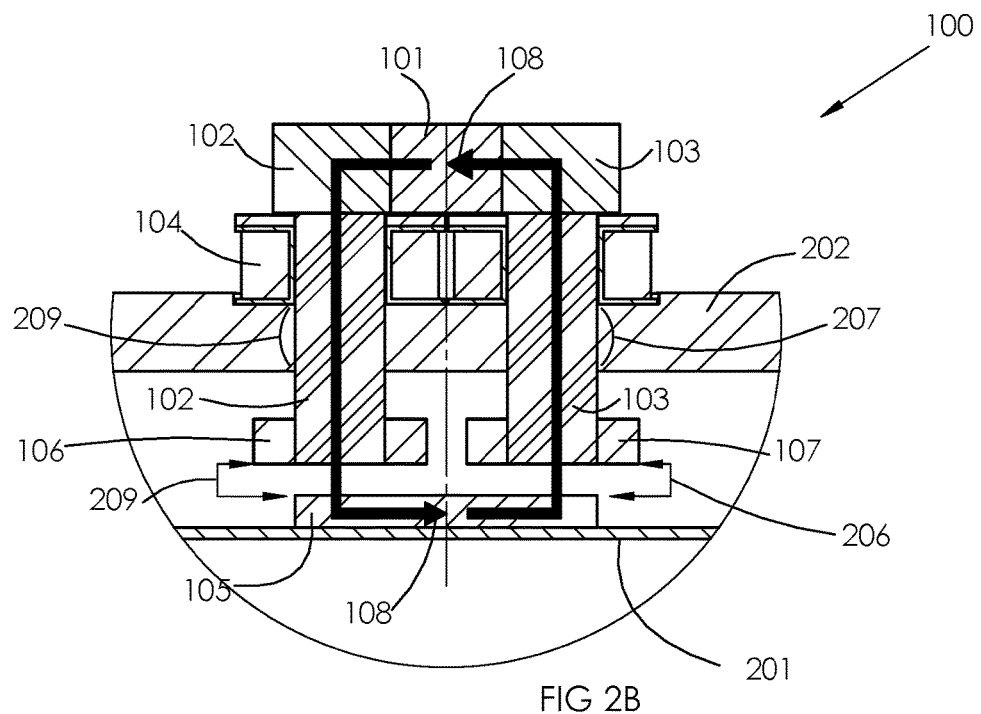
FIG. 2B is a close up cross section view of the example transducer assembly as shown in FIG. 2A.
Figure 2C:
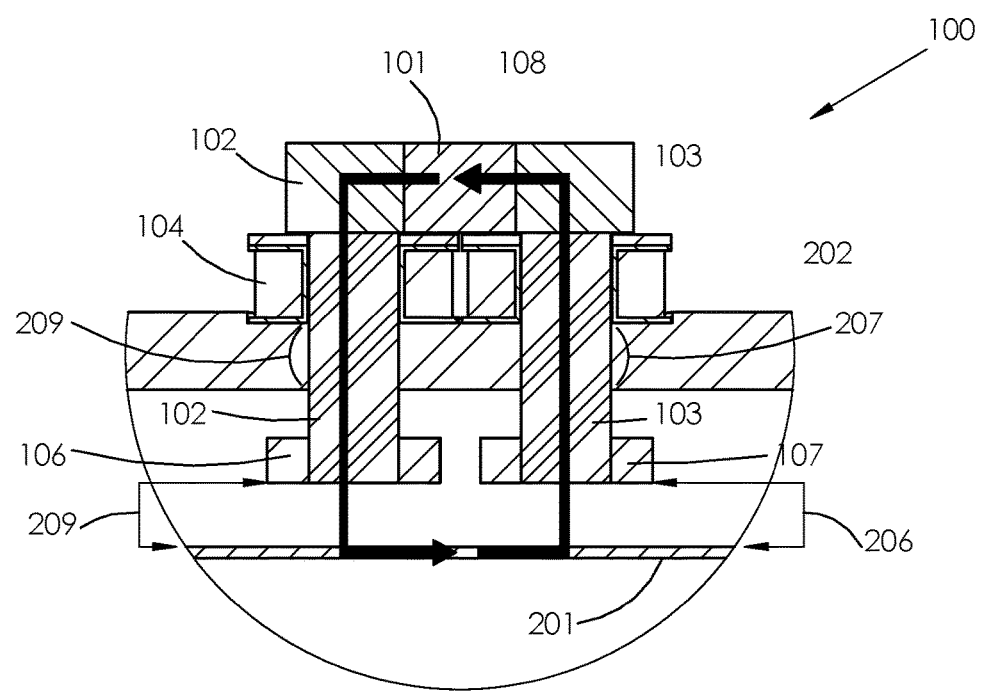
FIG. 2C is another example transducer assembly similar to that shown in FIG. 2B.

FIG. 2A is a cross section view of the example transducer assembly of FIG. 1 assembled into an immersed vibrating element type fluid parameter meter 200. FIG. 2B is a close up cross section view of the example transducer assembly 100 as shown in FIG. 2A. FIG. 2C is another example transducer assembly similar to that shown in FIG. 2B, where armature 105 of FIG. 2B has been removed, and armatures 102 and 103 have been elongated to reduce the size of gaps 205 and 206. This configuration includes vibrating element 201 (e.g., constructed with magnetically permeable material) as a third armature for the magnetic field 108.

Example transducer assembly 100 includes a permanent magnet 101 which may be, for example, a samarium cobalt type magnet due to its temperature stability, strength, and corrosion resistance. However, other types of magnets may be provided, including but not limited to neodymium iron boron, alnico, or others. Also, an electromagnet may be provided instead of a permanent magnet as further described hereinafter.

Example magnet 101 is magnetically associated at its north end with a first armature 102 comprised of magnetically permeable material such as 410 or 430 series stainless steel, carbon steel, High Permeability Alloy 49 or Alloy 80 by Carpenter Steel Corp., transformer iron, silicon iron, ferrite, and the like. Example armature 102 is configured to be of solid cross section, although this is not a requirement, and can be made of laminations of thin sheets, or by processes including machining, casting, powder metallurgy, and the like. Armature 102 passes through electrical coil 104 and is further elongated in area 209 to pass through and seal to a conduit wall 202 of the meter 200. Armature 102 can be further elongated to pass through a portion of the fluid flow area inside of the meter 200 to terminate near and in magnetic cooperation with armature 105 of FIG. 2B which is fixedly attached to the immersed vibrating element 201.

Example magnet 101 is also magnetically associated at its south end with a second armature 103 comprised of magnetically permeable material such as that just described for the first armature 102. Armature 103 is configured to be of solid cross section, although this is not a requirement. In other examples, the armature 103 can be made as laminated sheets or by processes including machining, casting, powder metallurgy, composite materials, and the like. Armature 103 passes through coil 104 and is further elongated in area 207 to pass through and seal to the conduit wall 202 of the meter 200. Armature 103 can be further elongated to pass through a portion of the fluid flow area inside of the meter 200 to terminate near and in magnetic cooperation with armature 105 of FIG. 2B which is fixedly attached to the immersed vibrating element 201. Armature 105 can have a rectangular or a "T" cross section shape or any other shape which reduces hydrodynamic drag and increases magnetic efficiency. Similarly, the upstream and downstream ends of armature 105 can be shaped to minimize hydraulic drag forces. Other shapes are anticipated including "U" shapes and others. Since armatures 102 and 103 do not touch armature 105, two gaps 205 and 206 are established there between through which magnetic field 108 passes (see FIG. 2B).

Armatures 102 and 103 and 105 can be shaped or sleeved or plated or coated as necessary to protect them from abrasion or corrosion. FIG. 10 shows shaped armature ends 106 and 107 having shaped ends facing upstream and downstream and rounded sides similar to the shape of a ship's hull, to minimize hydrodynamic drag which reduces abrasion from particles in the fluid. Sleeves or coatings or plating's such as nickel, tungsten carbide, ceramics, oxides, plastics, rubber, HMWPE (High Molecular Weight Poly Ethylene), and the like can be provided for this purpose. Also, armatures 102 and 103 can be sealed in areas 209 and 207 by threaded engagement, by sealant, by gaskets, by O-rings, by brazing, by welding, by adhesives, or by some other method.

Example, coil 104 can be one coil, or a plurality of separate coils or can be a plurality of coils electrically connected together in series or in parallel to form one coil. Both armatures 102 and 103 terminate near and in magnetic cooperation with a third armature 105 of FIG. 2B which is fixedly attached to immersed vibrating element 201 to transmit forces there between. In another example, if immersed vibrating element 201 is made of a magnetically permeable material such as 410 or 430 series stainless steel, carbon steel, PH17-4 steel, duplex steel, and the like, it can replace the magnetic functionality of third armature 105 and carry the magnetic field 108 through a portion of vibrating element 201, thereby becoming the third armature.

FIG. 2C shows another example assembly whereby armature 105 has been removed and the magnetic field 108 is being carried by a portion of vibrating element 201 thereby assuming the functionality of a third armature 105. In the assembly of FIG. 2C, armatures 102 and 103 have been extended across a portion of the fluid flow area of meter 200 to minimize the gaps 205 and 206. This extension allows for a more efficient configuration of vibrating element 201 without regard to the proximity of vibrating element 201 to outer conduit wall 202. This extension also allows for a smaller gap distance 205 and 206 which increases the magnitude of force that can be transmitted between armatures 102 and 103, and armature 105. Similarly, a smaller gap distance 205 and 206, increases the sensitivity of transducer assembly 100 when it is implemented as a motion sensor.

As can be seen in FIG. 2B, permanent magnet 101 causes a magnetic field 108 to circulate through armatures 102, 103, 105, and gaps 205 and 206. The magnetic field 108 passing through gaps 205 and 206 causes a pulling force between armature 105 (or vibrating element 201 if made of magnetic material) and armatures 102 and 103. This pulling force can be configured to be very strong as necessary to drive the vibration of the vibrating element 201 operating in high viscosity fluids.

Figure 3:
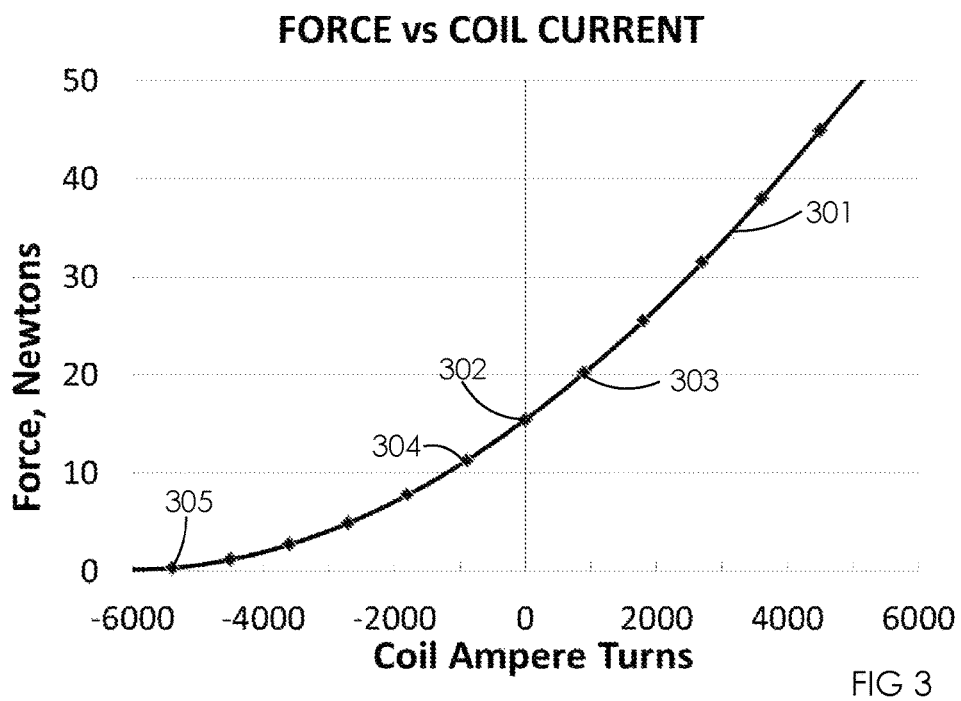
FIG. 3 is a graph illustrating a relationship between armature force and coil ampere turns.

FIG. 3 is a graph 301 illustrating a relationship between armature force and coil ampere turns. Graph 301 shows the relationship between Newtons of pulling force and the current through coil 104 in the units of ampere turns. For this specific example, at zero ampere turns of electrical current, there is a pulling force of about 16 Newtons due to the permanent magnetic field 108, shown as point 302. Applying positive electrical current of +1000 ampere turns increases the magnetic field 108 and increases the force to about 20 Newtons as shown by point 303. By applying negative current of about −1000 Ampere turns, the magnetic field 108 is decreased and thus the pulling force is decreased to about 12 Newtons as shown by point 304.

Figure 4:
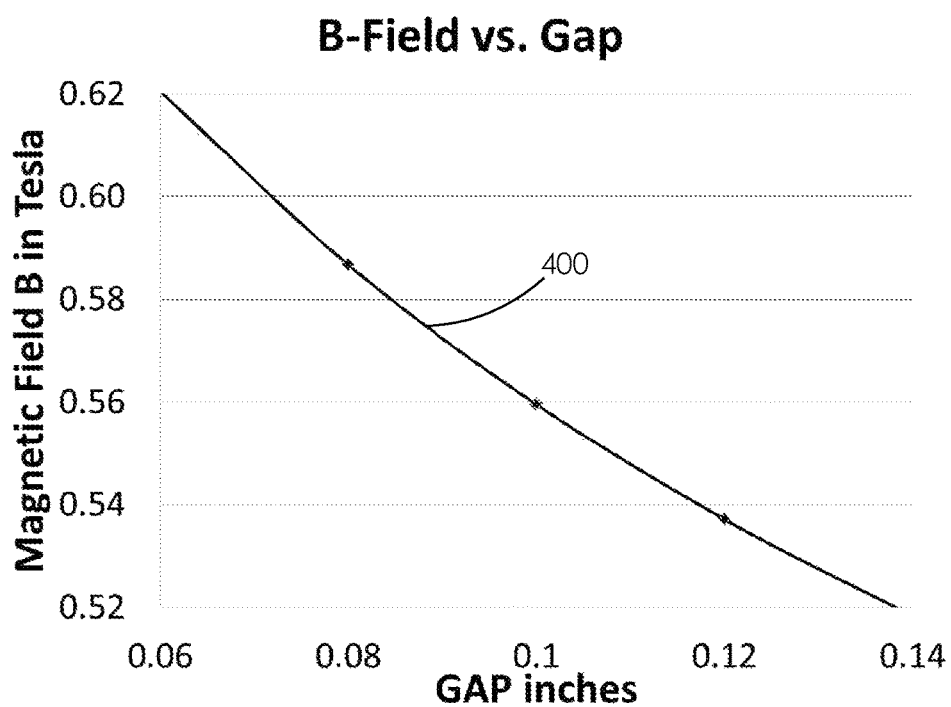
FIG. 4 is a graph illustrating a relationship between gap distance, and magnetic field through gaps.

FIG. 4 is a graph illustrating a relationship between gap distance 205 and 206, and magnetic field 108 through gaps 205 and 206. The graph 400 shows the relationship between magnetic field 108 in Tesla in armature 102 or 103 as a function of gap distance 205 and 206 in inches. Graph 400 shows that as the gap 205 and 206 increases in distance, the magnetic field 108 decreases in magnitude. Vibration of vibrating element 201 causes a sinusoidal time variation in the gap distance 205 and 206, and according to graph 400 this may cause a similar sinusoidal time variation in magnetic field 108 as gap 205 and 206 varied. According to Maxwell's equations, a time varying magnetic field causes a voltage in a coil placed around that varying field.

Since the time rate of change of magnetic field 108 is a sinusoidal function of the vibration frequency of vibrating element 201, the resulting voltage is also a sinusoid at the vibration frequency, having an amplitude proportional to the velocity of the vibrating element 201.

Figure 5:
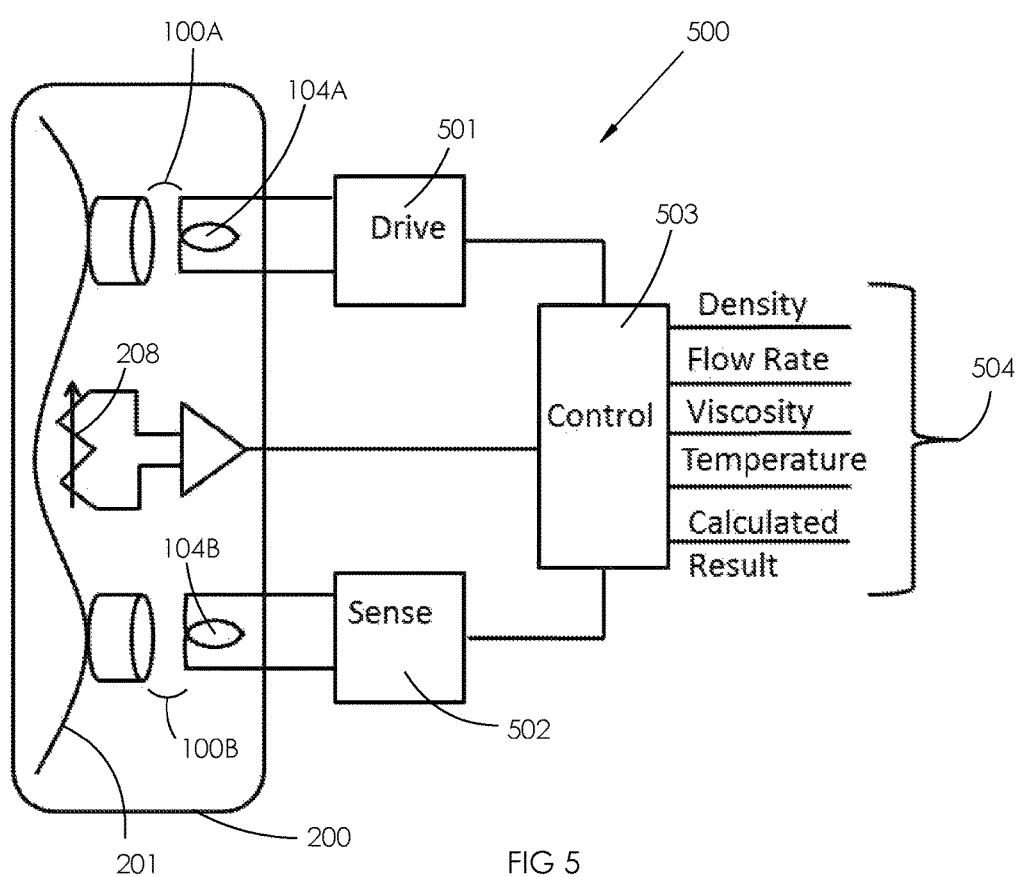
FIG. 5 is a block diagram of example control electronics.

FIG. 5 is a block diagram of example control electronics. The block diagram shows how a plurality of transducer assemblies 100A and 100B can be provided together in a complete meter 200 assembly.

Transducer 100A is the same as transducer 100 previously described but is here implemented as a vibration driver and is therefore designated as 100A. Transducer 100B is the same as transducer 100 previously described but is here implemented as a vibration sensor and is therefore designated as 100B.

To implement the transducer as a vibration sensor, the voltage across coil 104 may be measured by electronic sensing amplifier 502 in conjunction with electronic control module 503 of FIG. 5, as a representation of the vibration of vibrating element 201.

Therefore, transducer 100 can be implemented as a vibration sensor by measuring the voltage occurring in coil 104 with an electronic sense amplifier 502 in conjunction with an electronic control module 503, which measures a sinusoidal signal proportional to the vibration of vibrating element 201.

The example meter 200 of FIG. 5 is a vibrating element type fluid parameter meter where an immersed vibrating element 201 is caused to vibrate by electrical current excitation from electronic control module 503 in conjunction with drive amplifier 501 to coil 104A in transducer 100A here implemented as a vibration driver. The vibration thus caused on vibrating element 201 is sensed by transducer 100B and converted to an electrical signal indicative of vibration level in sensing amplifier 502 the signal being conveyed to electronic control module 503.

Both example amplifiers 501 and 502 are in electronic communication with control module 503 which receives vibration information from sensing amplifier 502, and causes vibration of vibrating element 201 to be maintained at a specified magnitude, and also implements the vibration information obtained from amplifiers 501 and 502 to derive fluid parameter outputs 504 such as density, flow rate, and viscosity as is known in the art. This type of meter 200 may include a temperature sensor 208, and therefore temperature is also an output parameter 504. Also other fluid parameter outputs 504 which can be calculated from those that are measured such as PPA ("pounds of propant added"), or GVF ("gas volume fraction"), net oil, volume concentration, mass concentration, flow rate, and others.

Before continuing, it should be noted that the examples described above are provided for purposes of illustration, and are not intended to be limiting. Other devices and/or device configurations may be utilized to carry out the operations described herein.

Figure 6A:
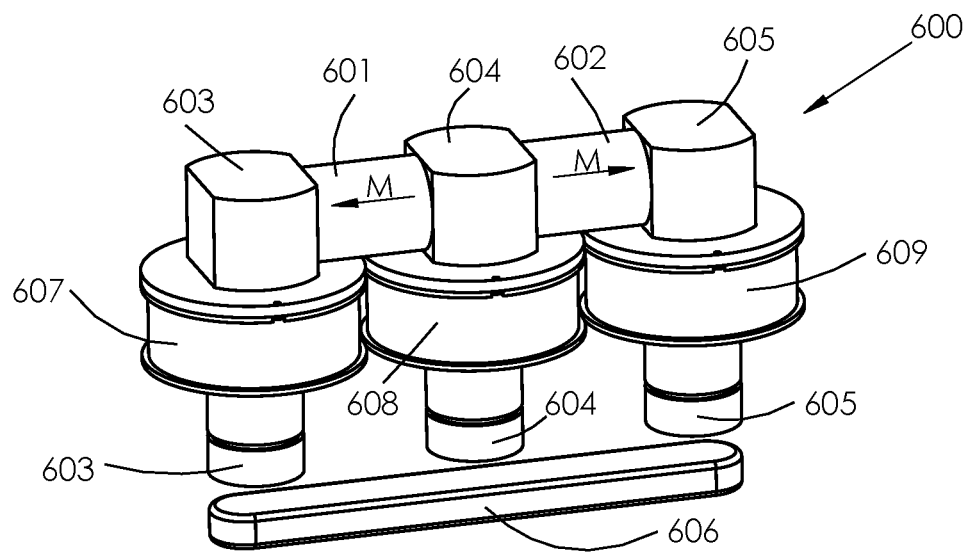
FIG. 6A is an isometric view of another example transducer assembly.
Figure 6B:
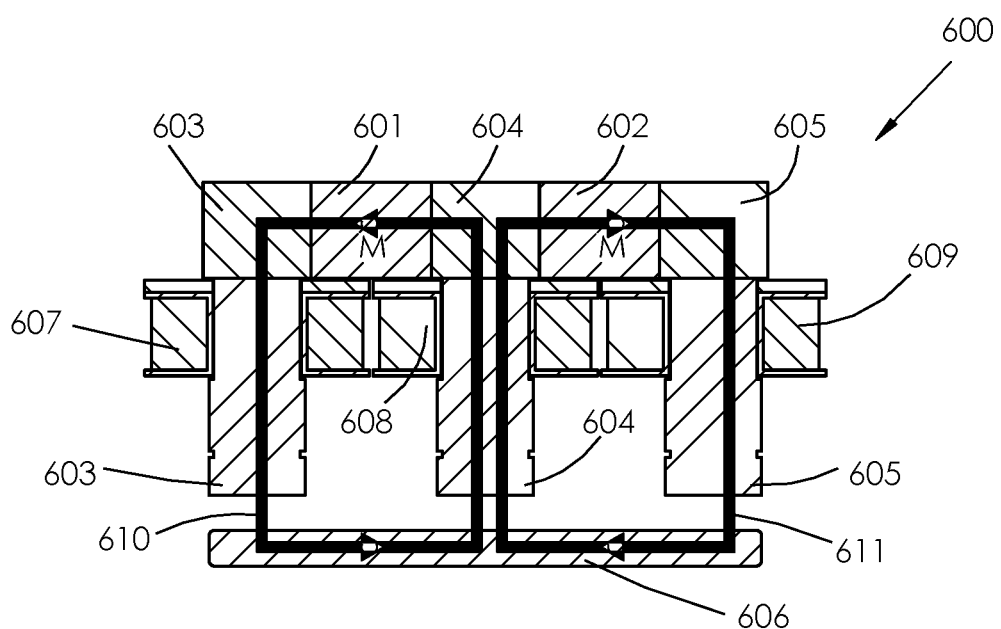
FIG. 6B is a cross section view of the example transducer assembly of FIG. 6A.

FIG. 6A is an isometric view of another example transducer assembly 600. FIG. 6B is a cross section view of the example transducer assembly 600 of FIG. 6A. In FIGS. 6A and 6B, the transducer assembly 600 employs two permanent magnets 601 and 602, and four armatures 603, 604, 605, and 606. Transducer 600 also employs three coils 607, 608, and 609. This arrangement of components creates two magnetic fields 610 and 611 which both pass through armature 606. While the example transducer 600 is physically more complicated than the example transducer 100, it is functionally the same but comprises a plurality of permanent magnets, and a plurality of armatures. One advantage gained by this configuration is rejection of electrical noise from extraneous electromagnetic fields.

In each of the above-described examples, the functionality of permanent magnets 101, 601 and 602 is to create a magnetic field. As an alternative to having a permanent magnet, an electromagnet may be provided and directly substituted for permanent magnet 101, or for magnets 601 and 602. In another example, electrical current from drive amplifier 501 through coil 104 may also cause a magnetic field similar to that of permanent magnet 101 and may therefore substitute for the permanent magnet 101 (not shown). Since permanent magnets require no electrical power source, it is more efficient to provide a permanent magnet, but as just stated it is not required.

Figure 7:
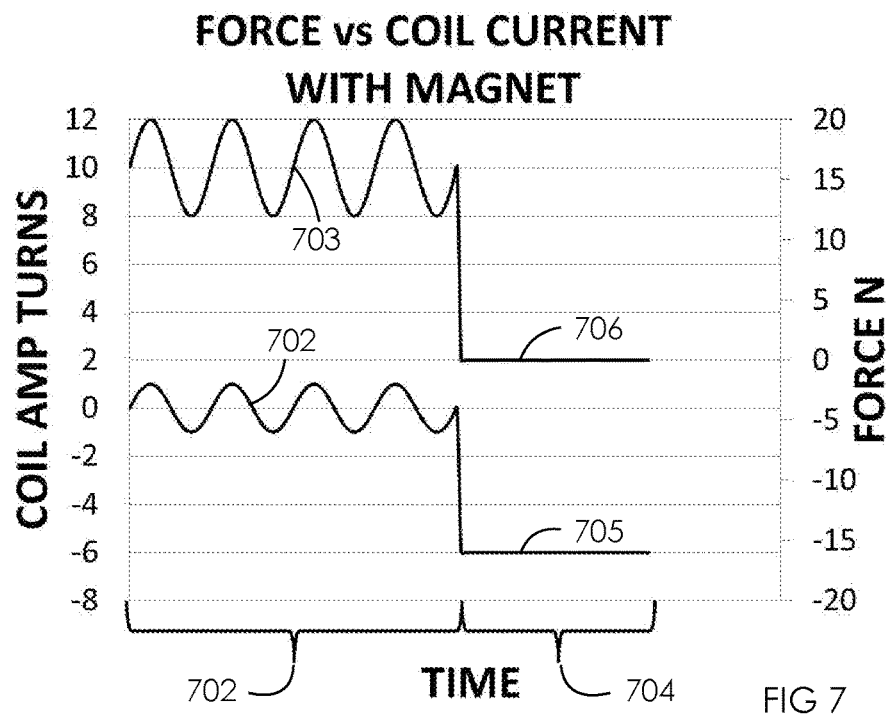
FIG. 7 is a graph illustrating coil current and resulting magnetic force versus time for both normal operation and during a self-cleaning period, with a permanent magnet in the magnetic circuit.

FIG. 7 is a graph illustrating coil current and resulting magnetic force versus time for both normal operation and during a self-cleaning period, with a permanent magnet in the magnetic circuit. The graph shows the relationship between coil current and armature force during a time of normal operation 701, and during a time of self-cleaning operation 704.

To implement the transducer 100 as a vibration driver during a time of normal operation 701, alternating electrical current 702 may be applied by an electronic control module 503 in conjunction with drive amplifier 501 of FIG. 5 to the one or more coils 104, causing an alternating magnitude of the magnetic field 108, and an alternating magnitude of the resulting pulling force 703. This alternating current 702 from electronic control module 503 in conjunction with drive amplifier 501 and its resulting alternating force 703 is normally synchronized in the appropriate phase and frequency with the desired natural vibration mode shape of the immersed vibrating element 201 to reinforce the natural vibration and to increase its amplitude and to maintain that amplitude at a prescribed value.

Another aspect is the ability to clean any adherent magnetic particles from armatures 102, 103, gaps 205 and 206, and armature 105 (or vibrating element 201 if made of magnetic material and armature 105 is eliminated). This cleaning method is accomplished by applying negative electrical current 705 from electronic control module 503 in conjunction with drive amplifier 501 in the amount of about −6000 ampere turns to coil 104 to cause magnetic field 108 and thus the force 706 between the armatures to go to near zero as shown by point 305 on graph line 301 of FIG. 3, and on the graph of FIG. 7. When the pulling force 706 is near zero as shown by point 305, there is nearly zero residual magnetic field 108 traversing gaps 205 and 206, and approximately no magnetic field to entrap magnetic particles to armature 105 (or to vibrating element 201 if armature 105 is replaced by vibrating element 201). Any entrapped magnetic particles may fall away or be washed away by any flowing fluid in meter 200.

Since applying negative 6000 ampere turns of electrical current 706 may cause heat buildup in coil 104 over time, this cleaning process may be done in a few seconds time, and during flowing fluid conditions, and only repeated as desired or based on the fluid conditions.

Figure 8:
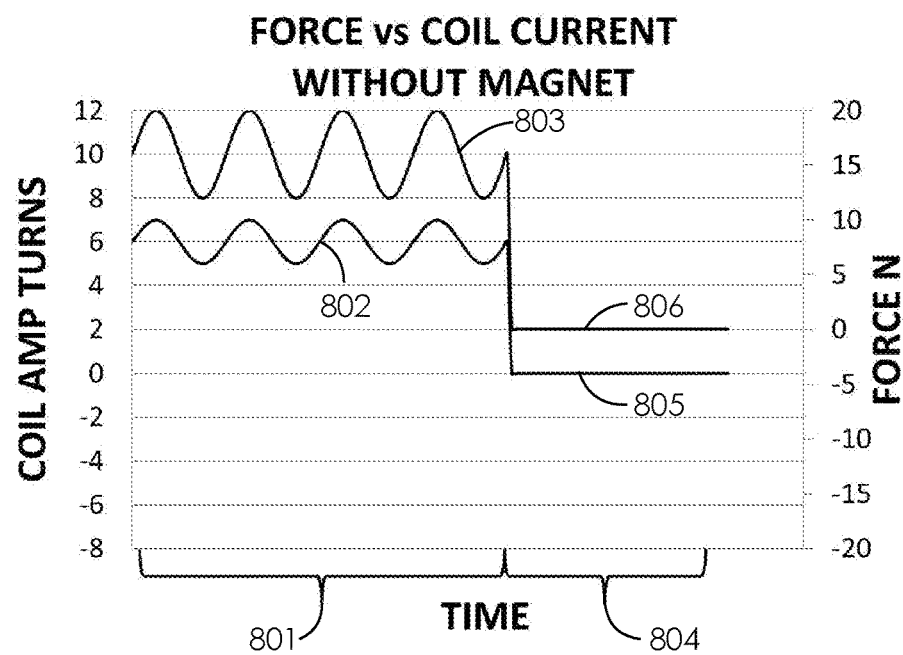
FIG. 8 is a graph illustrating coil current and resulting magnetic force versus time for both normal operation and during a self-cleaning period, without a permanent magnet in the magnetic circuit.

FIG. 8 is a graph illustrating coil current and resulting magnetic force versus time for both normal operation and during a self-cleaning period, without a permanent magnet in the magnetic circuit. The graph shows the relationship between coil current and armature force during a time of normal operation 801, and during a time of self-cleaning operation 804 but it differs from FIG. 7 in that FIG. 8 is for the situation without using a permanent magnet. During a time of normal operation 801, electrical current 802 is directed through coil 104 as a sine wave of amplitude 1000 ampere turns and an average value (a DC value) of 6000 ampere turns. This average value of 6000 ampere turns causes the same magnetic field 108 as earlier described, and the same armature force 803 as was just described as 703, but does so without a permanent magnet involved, and can therefore be described as an electromagnet.

During a self-cleaning period 804, the electrical current 805 is held at near zero ampere turns which causes the armature force 806 to also be near zero. During this period 804 there is nearly zero magnetic field 108 across gaps 205 and 206, and any adherent magnetic particles falls off or is washed away by any flowing fluid.

The application of electrical current 802 in coil 104 to create magnetic field 108 draws more energy than is needed when a permanent magnet is provided to create magnetic field 108 and is therefore less efficient.

Figure 9A:
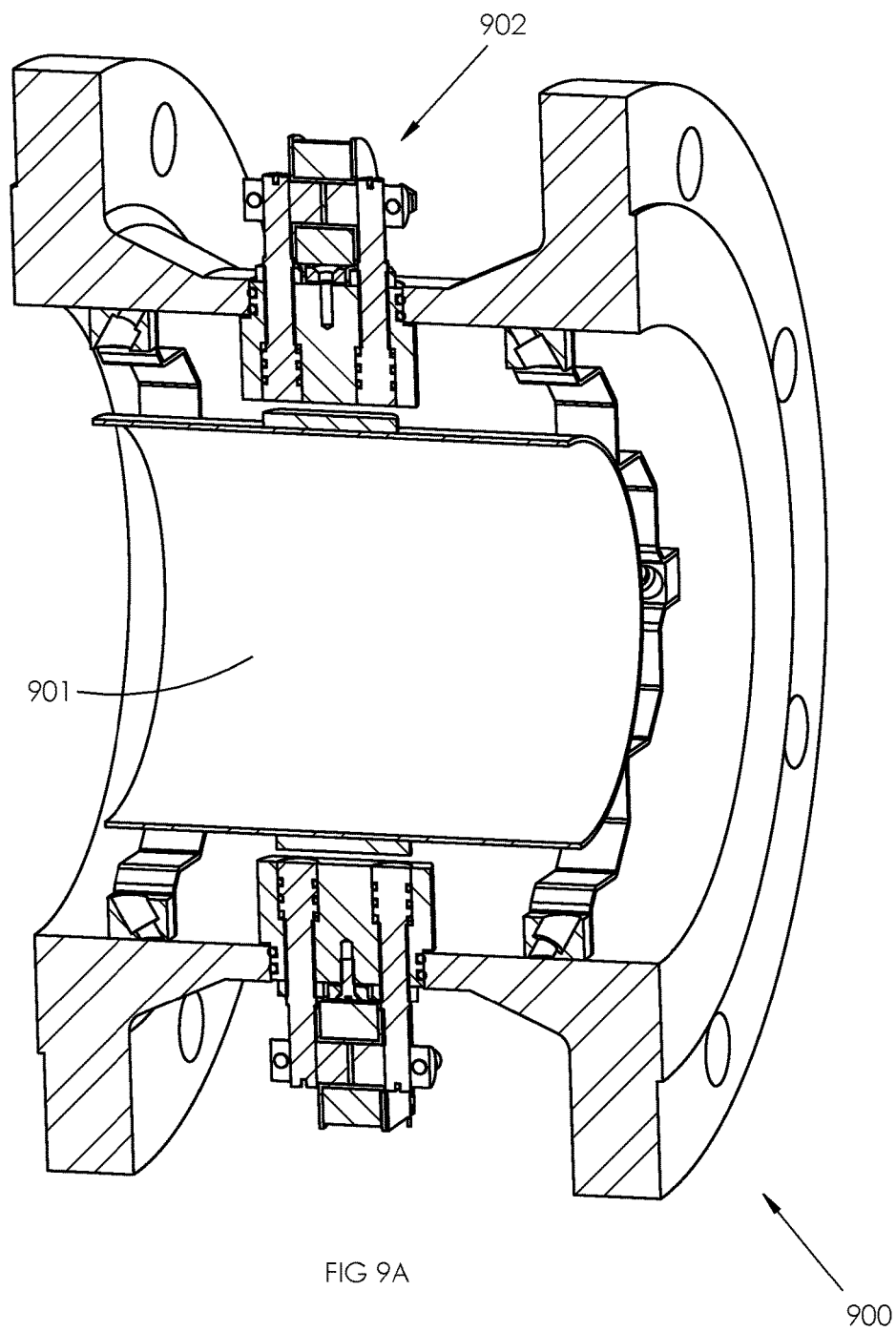
FIG. 9A is a cross section view of another example transducer assembly.
Figure 9B:
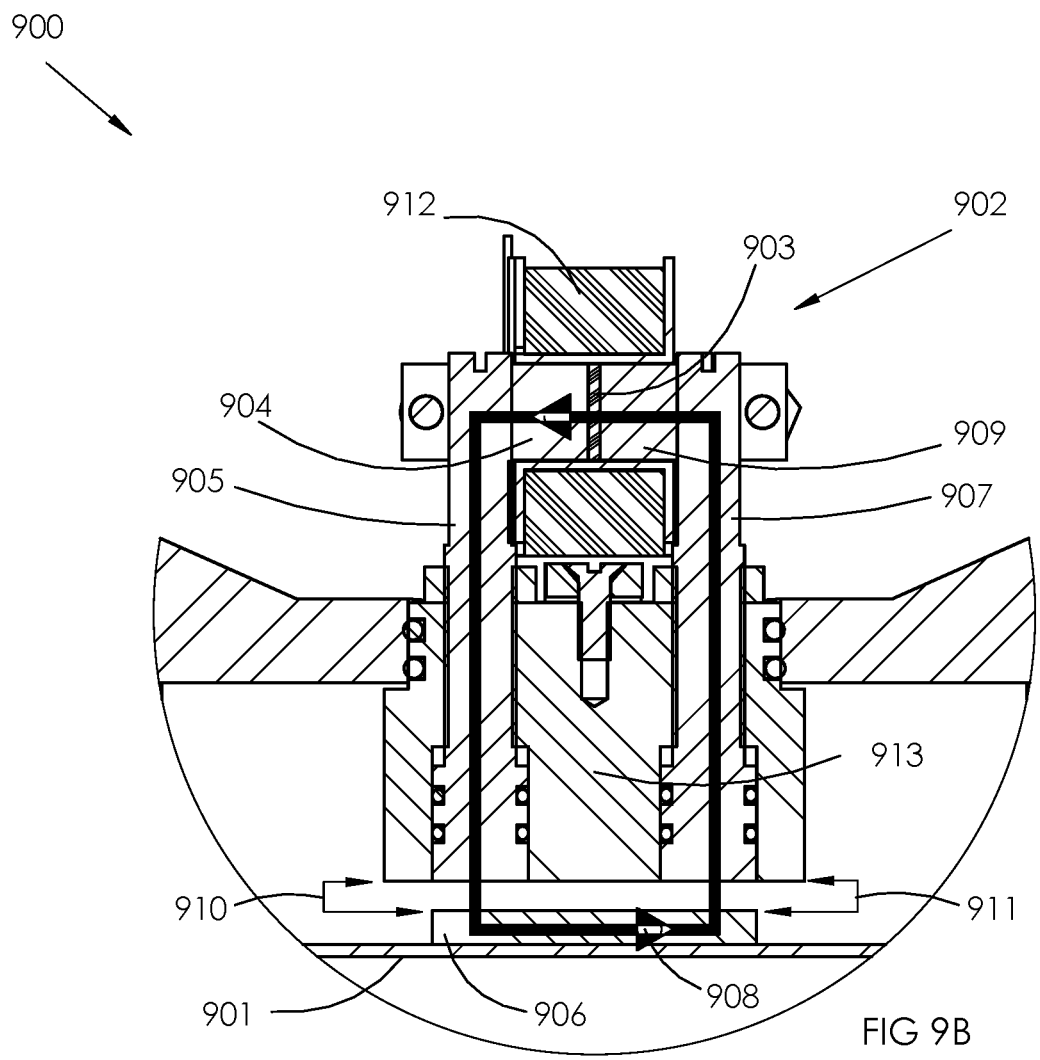
FIG. 9B is a close up cross section view of the example transducer assembly shown in FIG. 9A.
Figure 9C:
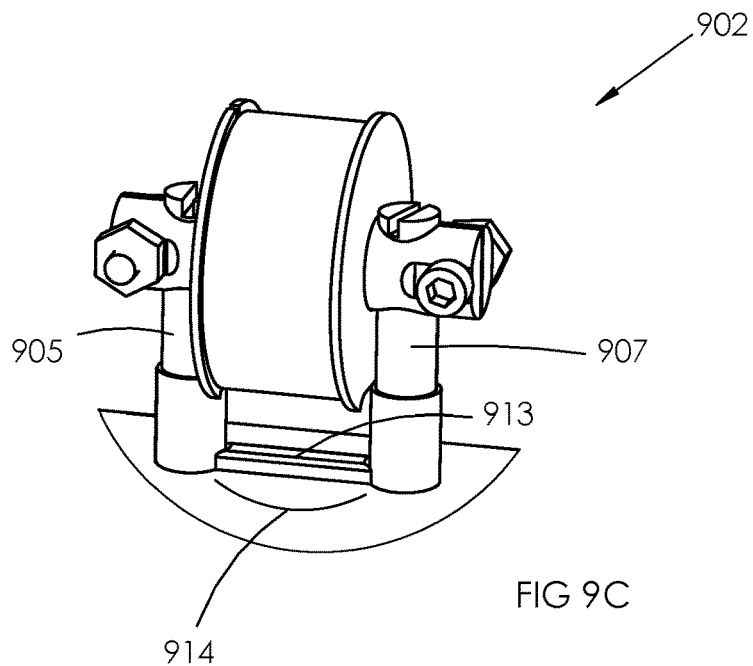
FIG. 9C is a view of another example transducer assembly, showing loss reduction.
Figure 9D:
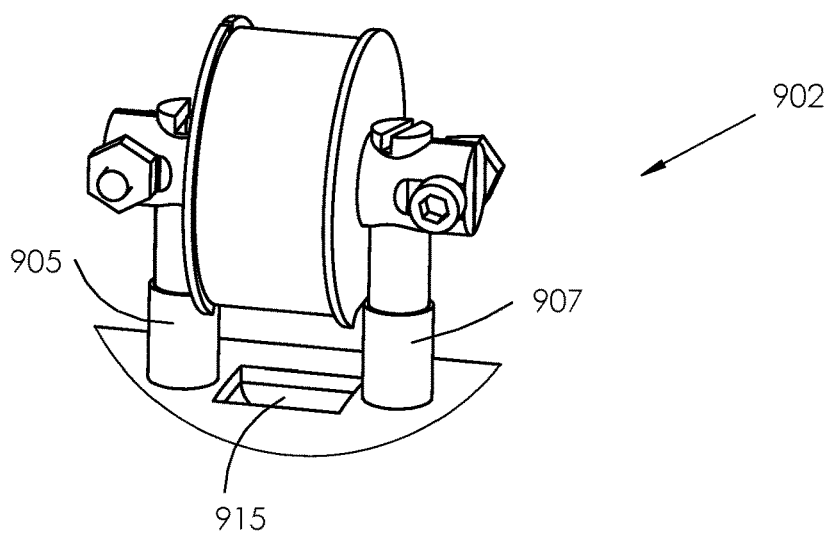
FIG. 9D is a view of another example transducer assembly, showing loss reduction.

Other arrangements of permanent magnets and armatures can be devised. FIG. 9A is a cross section view of another example transducer assembly including a vibrating element and an electromagnetic transducer, where the transducer armatures are adjustable, and are electrically and magnetically isolated from the outer conduit to reduce eddy current losses and improve efficiency. FIG. 9B is a close up cross section view of the example transducer assembly shown in FIG. 9A. FIG. 9C is a view of another example transducer assembly, showing loss reduction. FIG. 9D is a view of another example transducer assembly, showing loss reduction.

FIG. 9A is another example transducer assembly 900, where transducer assembly 902 is configured to reduce losses and be more efficient when implemented as a vibration driver, or a vibration sensor in conjunction with vibrating element 901. FIG. 9B is a close up view of the transducer assembly 902 showing the loss reduction methods and apparatus next described. Transducer assembly 902 is comprised of a magnetic circuit as earlier described for example transducers 100 and 600, but differs from those earlier examples, in that the armatures are adjustable thereby allowing for the adjustment their associated gap distances, and the material proximate the armatures is made of low or non-conductive material to reduce electrical (eddy-current) and or magnetic losses as now describe in detail.

Example transducer assembly 902 includes permanent magnet 903 whose north end is associated with armature 904 for the conveyance of magnetic field 908 therethrough. Permanent magnet 903 may be made from any suitable permanent magnet material as was earlier described, or may be replaced by an electromagnet also as earlier described.

Armature 904 is associated with adjustable armature 905 which conveys magnetic field 908 therethrough to gap 910. Armature 905 is adjustable in its position relative to gap 910 to allow for adjusting the distance of gap 910. Armature 906 is associated with vibrating element 901 and conveys magnetic field 908 therethrough and conveys any associated forces to vibrating element 901. Armature 907 also conveys magnetic field 908 from armature 906 to armature 909 and is adjustable in its position relative to gap 911 to allow for adjusting the distance of gap 911.

The adjustability of armatures 905 and 907 allow for adjusting gaps 910 and 911 which can be provided to adjust the magnitude of magnetic field 908. This adjustment is effective to increase or decrease the sensitivity of transducer 902 and can be provided to balance or match this sensitivity with other transducers on the assembly. Depending on transducer circuit configuration, some electrical noise immunity can be achieved through sensitivity balancing as just described. Armature 909 conveys magnetic field 908 from adjustable armature 907 back to the distal end of permanent magnet 903.

Example coil 912 is in magnetic communication with the magnetic circuit just described and is provided to convey electrical current therethrough which modifies magnetic field 908. Since armatures 905 and 907 do not touch armature 906, a force is created therebetween whenever magnetic field 908 is present.

When transducer 902 is implemented as a vibration driver electrical current is supplied to coil 912 to cause an alternating force on vibrating element 901 as was earlier described for example transducers 100 and 600. When transducer 902 is implemented as a vibration sensor, a voltage is sensed in coil 912 representing the vibratory motion of element 901 similar to earlier descriptions of example transducers 100 and 600.

Example loss reduction element 913 is configured to reduce electrical and or magnetic losses associated with example transducer 902 by increasing the electrical and or magnetic resistance in the area proximate to transducer assembly 902. Loss reduction element 913 may be made of an electrical insulting and or non-magnetic material such as ceramic, plastic, rubber, and the like. In addition, by encasing armatures 905 and 907 in a loss reduction element 913 made of abrasion resistant material such as HMWPE and the like, armatures 905 and 907 may be protected from abrasion by abrasive fluid motion.

By including loss reduction element 913, eddy-current losses, and or magnetic losses that might otherwise occur are reduced or eliminated thereby increasing the sensitivity and effectiveness of transducer assembly 902. The effectiveness of loss reduction element 913 can be approximated by creating a non-conductive slit in area 914 in the outer conduit between armatures 905 and 907 such as shown in FIG. 9C.

In an example, a slit in area 914 breaks the electrical conductivity between armatures 905 and 907 thereby reducing eddy-current losses. A slit in area 914 can be filled with a non-conductive material 913 for sealing purposes such as polymers, ceramic, plastic, epoxy, rubber and the like. Another method to achieve loss reduction is to remove electrically or magnetically conductive material proximate to transducer assembly 902.

FIG. 9D shows an example of transducer assembly 902 where material of the outer conduit has been removed in the area 915 as shown. This removal of material reduces the electrical conductivity and magnetic permeability thereby reducing losses. This material removal can be accomplished by machining, by casting, by drilling and the like. The area 915 is most effective when placed between armatures 905 and 907, but can also be outside of area 915.

Figure 10A:
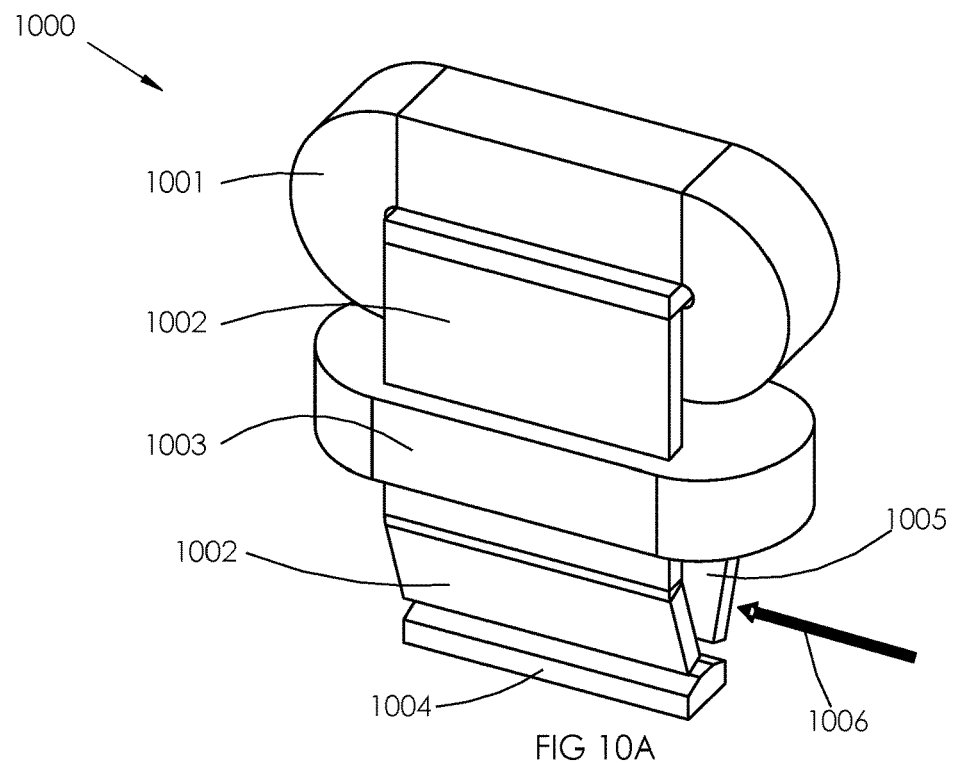
FIG. 10A is an oblique view of another example transducer assembly where the armatures are generally flat in shape, and aligned with the direction of fluid flow to reduce hydrodynamic drag.
Figure 10B:
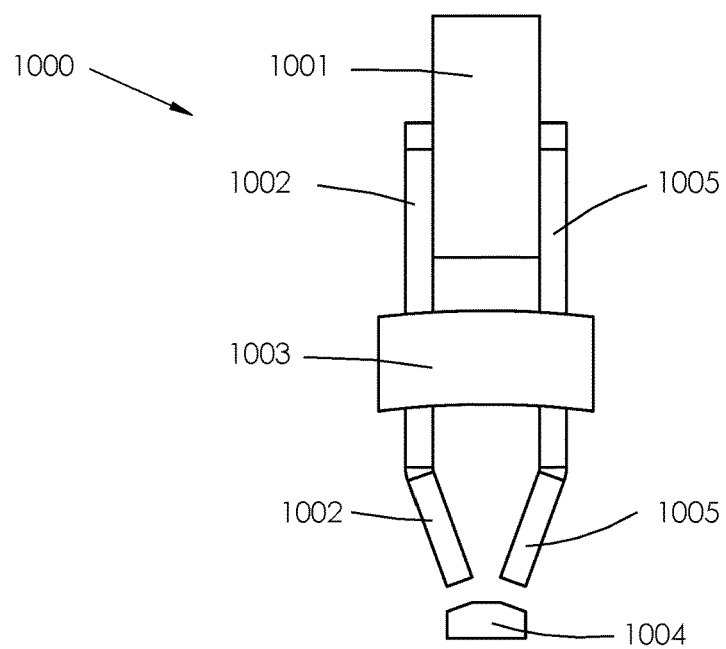
FIG. 10B is a view of the example transducer assembly of FIG. 10A looking in the direction of fluid flow.

FIG. 10A is an oblique view of another example transducer assembly 1000 where the armatures are generally flat in shape, and aligned with the direction of fluid flow to reduce hydrodynamic drag. FIG. 10B is a view of the example transducer assembly of FIG. 10A looking in the direction of fluid flow.

Example transducer assembly 1000 includes coil 1001, armatures 1002, and 1005 which are generally thin and flat in shape and aligned parallel with the direction of flow 1006 to minimize hydrodynamic drag forces. Armatures 1002 and 1005 pass through the wall of the outer pipe 1003 as in previous examples, to deliver magnetic fields to moving armature 1004 which is mounting on a vibrating element (not shown).

It is noted that the examples shown and described are provided for purposes of illustration and are not intended to be limiting. Still other examples are also contemplated.

The invention claimed is:

1. An electromagnetic transducer for a fluid parameter meter, comprising:
   at least one permanent magnet establishing a magnetic field;
   a first armature mounted to, and in magnetic cooperation with the permanent magnet;

a second armature mounted to, and in magnetic cooperation with, the permanent magnet;

wherein the first and the second armatures are arranged to interact with a third armature in magnetic cooperation with the first armature and the second armature;

at least one electric coil mounted to either of the first or second armature in cooperation with the magnetic field so that electric current through the electric coil is effective to vary vibratory forces;

wherein the third armature is mounted in association with a vibrating element, or comprising a portion of the vibrating element itself, and in magnetic cooperation with the first armature and the second armature through a first gap and a second gap to allow the transmission of the vibratory forces between the third armature, and the second armature and the first armature; and an electronic module to control the electric current and the vibratory forces on a vibrating element of the fluid parameter meter.

2. An electromagnetic transducer for causing vibratory forces on a vibrating element in a vibrating element type fluid parameter meter including an outer conduit to convey a fluid and the vibrating element being immersed in the fluid, comprising:

at least one permanent magnet mountable in association with the outer conduit, to create a magnetic field;

a first armature, made of magnetically permeable material, mounted to and in magnetic cooperation with, the permanent magnet to convey and shape the magnetic field from the permanent magnet through a wall of the outer conduit in a first location to a first gap;

a second armature, made of magnetically permeable material, mounted to, and in magnetic cooperation with, the permanent magnet to convey and shape the magnetic field from the permanent magnet through a wall of the outer conduit in a second location to a second gap;

wherein the first and the second armatures arranged to interact with a third armature, made of magnetically permeable material, mountable in association with the vibrating element, or comprising a portion of the vibrating element itself, and in magnetic cooperation with the first armature and the second armature through the first gap and the second gap, to allow the transmission of the vibratory forces between the third armature, and the second armature and the first armature;

at least one electric coil mounted to either or both of the first and second armature in cooperation with the magnetic field so that electric current through the electric coil to vary the vibratory forces; and an electronic module to control the electric current of the transducer to thereby control the vibratory forces on the vibrating element.

3. The transducer of claim 2, wherein the electronic module causes the electric current through the at least one electric coil to cause the magnetic field to be reduced to near zero, to cause the release of adherent magnetic particles from any of the first armature or the second armature or the third armature.

4. The transducer of claim 2, wherein any of the first armature or the second armature or the third armature are shaped to minimize damage from abrasion or corrosion.

5. The transducer of claim 2, wherein the third armature comprises a portion of the vibrating element.

6. The transducer of claim 2, wherein the first armature and the second armature are sealed through a wall of the outer conduit to prevent leakage of the fluid using a method selected from at least one of the following: threaded engagement, O-ring, sealant, welding, brazing, and adhesive.

7. The transducer of claim 2, wherein the functionality of the permanent magnet is replaced by an electromagnet.

8. An electromagnetic transducer for sensing the vibration of a vibrating element in a fluid parameter meter including an outer conduit to convey a fluid, comprising:

at least one permanent magnet mounted in association with the outer conduit, to create a magnetic field;

a first armature, made of magnetically permeable material, mounted in magnetic cooperation with, the permanent magnet to convey and shape the magnetic field from the permanent magnet through a wall of the outer conduit in a first location to a first gap;

a second armature, made of magnetically permeable material, mounted in magnetic cooperation with, the permanent magnet to convey and shape the magnetic field from the permanent magnet through a wall of the outer conduit in a second location to a second gap;

wherein the first and second armatures being arranged to interact with a third armature, made of magnetically permeable material, mountable in association with the vibrating element, or comprising a portion of the vibrating element itself, and in magnetic cooperation with the first armature and the second armature through the first gap and the second gap respectively so that the vibration of a the vibrating element causes variations in the magnetic field;

at least one electric coil mounted to either or both of the first and second armature in cooperation with the magnetic field so that the variations in the magnetic field cause electric signals in the electric coil; and an electronic module configured to measure the electric signals and produce an output signal representative of the vibration of the vibrating element.

9. The transducer of claim 8, wherein the electronic module is configured to supply the electric current through the at least one electric coil to cause the magnetic field to be reduced to near zero, to cause the release of adherent magnetic particles from any of the first armature or the second armature or the third armature.

10. The transducer of claim 8, wherein any of the first armature or the second armature or the third armature are coated or plated or sleeved or shaped to prevent damage from abrasion or corrosion.

11. The transducer of claim 8, wherein the third armature comprises a portion of the vibrating element.

12. The transducer of claim 8, wherein the first armature and the second armature are sealed through a wall of the outer conduit to prevent leakage of the fluid using a method selected from at least one of the following: threaded engagement, O-ring, sealant, welding, brazing, and adhesive.

13. The transducer of claim 8, wherein the functionality of the permanent magnet is replaced by an electromagnet.

14. An electromagnetic transducer for causing or sensing vibratory forces on a vibrating element in a vibrating element type fluid parameter meter including an outer conduit to convey a fluid and the vibrating element being immersed in the fluid, comprising:

at least one permanent magnet mountable in association with the outer conduit, to create a magnetic field; and a first armature, made of magnetically permeable material, mounted in magnetic cooperation with, the permanent magnet to convey and shape the magnetic field from the permanent magnet through a wall of the outer conduit in a first location to a first gap; and a second armature, made of magnetically permeable material, mounted in magnetic cooperation with, the permanent magnet to convey and shape the magnetic field from the permanent magnet through a wall of the outer conduit in a second location to a second gap;

wherein the first armature and the second armature being arranged such that, when the at least one permanent magnet is mounted in association with the outer conduit, the first armature and the second armature extend through the wall of the outer conduit so that the first location of the first armature and the second location of the second armature are proximate to a third armature that is part of the meter, the first and second armatures being separated from the third armature at the first and second locations by respective first and second gaps, the third armature being made of magnetically permeable material, mountable in association with the vibrating element, or comprising a portion of the vibrating element itself, such that the third armature may be in magnetic cooperation with the first armature and the second armature through the first gap and the second gap, to allow the transmission of the vibratory forces between the third armature, and the second armature and the first armature; and at least one electric coil mounted to either or both of the first and second armature in cooperation with the magnetic field so that electric current through the electric coil configured to vary or sense the vibratory forces.

15. The transducer according to claim 14, further comprising an electronic module configured to control the electric current of the transducer to thereby control or sense the vibratory forces on the vibrating element.

16. The transducer of claim 14, further comprising a loss reduction element effective to reduce eddy-current or magnetic losses.

17. The transducer of claim 14, wherein the first or the second gaps are adjustable.

18. The transducer of claim 14, wherein one transducer of a transducer pair generates vibrations within the fluid, and a second transducer of the transducer pair measures the vibrations.

19. The transducer of claim 18, wherein a control circuit sends commands to the vibration-generating transducer, receives measurements from the vibration-measuring transducer, interprets the measurements to yield one or more parameters of the fluid, and reports a result.

20. The transducer of claim 19, wherein the measured parameter is one or more of density, flow rate, viscosity, and temperature.

* * * * *